United States Patent [19]

Noel et al.

[11] Patent Number: 5,032,122
[45] Date of Patent: Jul. 16, 1991

[54] LOOP FASTENING MATERIAL FOR FASTENING DEVICE AND METHOD OF MAKING SAME

[75] Inventors: John R. Noel, Cincinnati; Charles L. Scripps, Blue Ash, both of Ohio

[73] Assignee: The Procter & Gamble Company, Cincinnati, Ohio

[21] Appl. No.: 355,065

[22] Filed: May 17, 1989

Related U.S. Application Data

[62] Division of Ser. No. 40,520, Apr. 24, 1987, abandoned.

[51] Int. Cl.$^5$ .............................................. A61F 13/16
[52] U.S. Cl. ................................... 604/391; 604/386; 24/442
[58] Field of Search ................... 604/391, 386; 24/442, 24/445, 448, 451; 128/DIG. 15

[56] References Cited

U.S. PATENT DOCUMENTS

| | | |
|---|---|---|
| 1,917,456 | 7/1933 | Mickelson . |
| 2,021,352 | 11/1935 | Eustis . |
| 2,434,111 | 1/1948 | Hawley, Jr. et al. . |
| 3,245,407 | 4/1966 | Mason . |
| 3,577,607 | 5/1971 | Ikoma . |
| 3,639,917 | 2/1972 | Althouse . |
| 3,715,415 | 2/1973 | Erb . |
| 3,860,003 | 1/1975 | Buell . |
| 3,913,183 | 10/1975 | Brumlik ................................ 24/450 |
| 3,943,981 | 3/1976 | De Brabander . |
| 3,955,575 | 5/1976 | Okuda ........................ 128/DIG. 15 |
| 3,959,051 | 5/1976 | Schirmer . |
| 4,303,571 | 12/1981 | Jansen et al. ........................ 524/426 |
| 4,429,002 | 1/1984 | Fukada et al. . |
| 4,515,595 | 5/1985 | Kievit et al. . |
| 4,531,999 | 7/1985 | Persson et al. . |
| 4,537,591 | 8/1985 | Coates ................................... 604/391 |
| 4,543,154 | 9/1985 | Reiter . |

(List continued on next page.)

FOREIGN PATENT DOCUMENTS

| | | |
|---|---|---|
| 0233364A2 | 8/1987 | European Pat. Off. . |
| 0258015 | 3/1988 | European Pat. Off. ............... 24/442 |
| 0341993A1 | 11/1989 | European Pat. Off. . |
| 2504242 | 8/1976 | Fed. Rep. of Germany ........ 24/445 |
| 59-88903 | 5/1984 | Japan . |

OTHER PUBLICATIONS

Japanese Patent Application No. 59-88903, Laid Open May 12, 1984.

Primary Examiner—C. Fred Rosenbaum
Assistant Examiner—Mark O. Polutta
Attorney, Agent, or Firm—Jeffrey V. Bamber; Steven W. Miller; Richard C. Witte

[57] ABSTRACT

A loop fastening material having a backing of orientable material and a multiplicity of fibrous elements extending from the backing. The fibrous elements are formed by filaments positioned on the backing and secured to the backing when the orientable material of the backing is in its dimensionally unstable state. The filaments are preferably positioned on the backing parallel to each other and essentially parallel to the path of response of the orientable material. The filaments are intermittently secured to the backing at spaced, fixed regions along the filaments so that each pair of fixed regions defines therebetween an unsecured catching region. Thus, the fibrous elements are formed by the shirring of the filaments at the catching regions when the orientable material is caused to be transformed to its dimensionally stable state such that it is caused to contract or gather along its path of response.

The loop fastening material is formed by a method comprising the steps of:
providing a backing of orientable material in its dimensionally unstable state;
positioning a plurality of filaments on the backing;
securing the filaments to the backing at spaced, fixed regions along each of the filaments, the fixed regions defining between each pair an unsecured catching region; and
causing the orientable material to be transformed along its path of response to its dimensionally stable state thereby shirring the filaments at the catching regions to form fibrous elements projecting from the backing between the fixed regions.

37 Claims, 3 Drawing Sheets

U.S. PATENT DOCUMENTS

| | | |
|---|---|---|
| 4,582,740 | 4/1986 | Zurcher et al. |
| 4,600,618 | 7/1986 | Raychok et al. ............... 428/92 |
| 4,604,315 | 8/1986 | McCall et al. |
| 4,606,694 | 8/1986 | Wideman . |
| 4,640,859 | 2/1987 | Hansen et al. |
| 4,654,246 | 3/1987 | Provost et al. ............... 428/88 |
| 4,714,735 | 12/1987 | Hodgson et al. ............... 525/514 |
| 4,725,473 | 2/1988 | Van Gompel et al. . |
| 4,732,631 | 3/1988 | Shimizu ............... 156/73.3 |
| 4,846,815 | 7/1989 | Scripps . |
| 4,894,060 | 1/1990 | Nestegard ............... 604/391 |
| 4,920,617 | 5/1990 | Higashinaka ............... 24/442 |

LOOP FASTENING MATERIAL FOR FASTENING DEVICE AND METHOD OF MAKING SAME

This is a division of application Ser. No. 040,520, filed on Apr. 24, 1987 abandoned.

FIELD OF THE INVENTION

The present invention relates to a loop fastening material for fastening devices, and more particularly, to a low-cost loop fastening material and a method for producing such a loop fastening material from an orientable material and filaments.

BACKGROUND OF THE INVENTION

Fastening devices such as hook and loop-type fasteners are known and have gained wide acceptance. Such materials are generally known by the tradename 'Velcro' and are generally described in U.S. Pat. Nos. 2,717,437; 3,009,235; 3,266,113; 3,550,837; and 4,169,303. The hook and loop-type fastener comprises two mating fastening materials wherein a hook fastening material engages a loop fastening material. Engagement of the complementary mating hook and loop fastening materials will occur by placing the surface defined by the hook in face to face relationship with the surface defined by the loop. The fastener resists separation by shear stress and certain peel forces applied to the fastener during use but are readily separable by peel forces applied substantially normal to the plane of their engagement.

Such fastening devices have been found especially useful and favorable on disposable articles such as disposable garments, disposable diapers, disposable packages, cartons and the like. While such fastening devices provide a secure closing means, their use has, however, been limited on disposable articles due to the fact that such fastening devices are relatively costly. The major reason that such fastening devices are too costly is that they have high manufacturing costs. Thus, there is a need for a low-cost fastening device for such disposable articles.

While many attempts have been made to provide a low-cost fastening device, most of the efforts have been directed toward developing a low-cost hook fastening material. The loop fastening material remains a costly element for a fastening device for disposable articles. Loop fastening materials typically have a number of woven loops extending outwardly from a backing. The loops may be provided by weaving a base fabric containing supplementary warp threads or by knitting. However, these processes produce generally costly loop fastening materials due to the fact that these processes are relatively slow.

Thus, it is an object of the present invention to provide an improved fastening device for disposable articles.

It is another object of the present invention to provide an improved loop fastening material.

It is a further object of the present invention to provide a loop fastening material which may be formed by positioning a plurality of filaments on a backing to form a low-cost loop fastening material.

It is a still further object of the present invention to provide a low-cost and improved method for producing a loop fastening material.

These and other objects of the present invention will be more readily apparent when considered in reference to the following description and when taken in connection with the accompanying drawings.

SUMMARY OF THE INVENTION

The present invention provides a loop fastening material having a backing of orientable material and a multiplicity of fibrous elements extending from the backing. The fibrous elements are formed by continuous filaments positioned on the backing and secured to the backing when the orientable material of the backing is in its dimensionally unstable state. The filaments are preferably positioned on the backing parallel to each other and essentially parallel to the path of response of the orientable material. The filaments are intermittently secured to the backing at spaced, fixed regions along the filaments so that each pair of fixed regions defines therebetween an unsecured catching region. Thus, the fibrous elements are formed by the shirring of the filaments at the catching regions when the orientable material is caused to be transformed to its dimensionally stable state such that it is caused to contract or gather along its path of response.

The loop fastening material is formed by a method comprising the steps of:

providing a backing of orientable material in its dimensionally unstable state;

positioning a plurality of filaments on the backing;

securing the filaments to the backing at spaced, fixed regions along each of the filaments, the fixed regions defining between each pair an unsecured catching region; and causing the orientable material to be transformed along its path of response to its dimensionally stable state thereby shirring the filaments at the catching regions to form fibrous elements projecting from the backing between the fixed regions.

The present invention also relates to a fastening device having a hook fastening material and a loop fastening material. The loop fastening material comprises the improved loop fastening material of the present invention. The hook fastening material comprises any of the well known hook fastening materials as are known in the art and which have a base and a number of engaging elements extending from the base. The loop fastening material and the complementary hook fastening material provide a secure closing means that will resist shear stress and peel forces encountered during use.

The present invention also relates to disposable articles and more particularly to a disposable diaper having such an improved fastening device.

DETAILED DESCRIPTION OF THE INVENTION

In the present invention, an orientable material is used as a backing for the loop fastening material. As used herein, the term "orientable material" refers to a web or film that has a dimensionally unstable state relative to some other dimensionally stable state and which can be caused to be transformed from the unstable to the stable state along a path of response by the removal of forces acting on the web or film or by the application of any form of energy or by any other convenient treatment.

Orientable materials of the type useful in the present invention include a number of materials well known to those skilled in the art. For example, the polyurethane described in U.S. Pat. No. 3,912,565 issued to Koch et al. on Oct. 14, 1975; the heat recoverable material described in U.S. Pat. No. 3,639,917 issued to Althouse on Feb. 8, 1972; and the plasticized vinyl chloride described in U.S. Pat. No. 3,819,401 issued to Massengale et al. on Jun. 25, 1974 can be used as the backing in the present invention.

Since the most convenient and practical form of energy to transform the orientable material is heat, preferred orientable materials are heat-shrinkable materials having a dimensionally heat stable state and a dimensionally heat unstable state and which contract at least uni-directionally from the heat unstable to the heat stable state along a path of response. These types of films are typically converted to a dimensionally heat unstable state via molecular orientation by laterally stretching it while at an elevated temperature which is less than its crystalline melting temperature and allowing it to cool. (This is generally done by means of a tentering apparatus.) When cooled, the polymers of the film are predominantly uni-axially oriented and the film essentially retains its new dimension until such time as it is again subjected to an elevated temperature where it recovers to its heat stable state. The film is thus in a heat unstable state. Specific film-forming compositions which are described as being suitable for forming webs capable of exhibiting heat stable and heat unstable states are disclosed in U.S. Pat. No. 4,303,571 issued to Jansen et al. on Dec. 1, 1981 and U.S. Pat. No. 4,543,154 issued to G. Reiter on Sep. 24, 1985, both of which are incorporated herein by reference.

Preferred heat-shrinkable materials include ethyl vinyl acetate copolymers, polystyrene-polyolefin block copolymers, ethylacrylate methacrylate copolymers and numerous other thermoplastic heat-sealable polymers as are known in the art. One particularly preferred heat-shrinkable material is a film comprising a blend of ethylene propylene rubber with ethyl vinyl acetate, such as that available from Exxon Chemical Company of Florham Park, N.J.

Alternatively, the orientable material of the backing may comprise an elastic or elastomeric material having an elongated orientation and a relaxed orientation and which contracts from its elongated orientation to its relaxed orientation along at least one path of response. These type of materials are typically converted to the elongated orientation by tensional forces applied in any manner along at least one axis of the film or web of the material and which when the tensional forces are removed, contracts along its path of response to its relaxed orientation, the material recovering a substantial proportion of its elongation. The elastomeric materials useful to form the backing thus include all suitable elastic materials capable of forming such an elastomeric backing. Elastomeric materials suitable for use herein include butadiene/acrylonitrile copolymers, styrene/isoprene copolymers, polyurethane elastomers, elastomeric films such as Kraton, natural rubber, or ethylene propylene-dimonomers.

The orientable materials of the present invention have been described in terms of having a dimensionally unstable state that is later transformed to its dimensionally stable state. While, in general, the dimensionally stable state is an absolute state, it is not necessary that it be. It is only required that the state following treatment be relatively more stable than the state preceeding treatment and that the state following treatment be sufficiently stable for practical use of the resultant loop fastening material.

Figure 3:
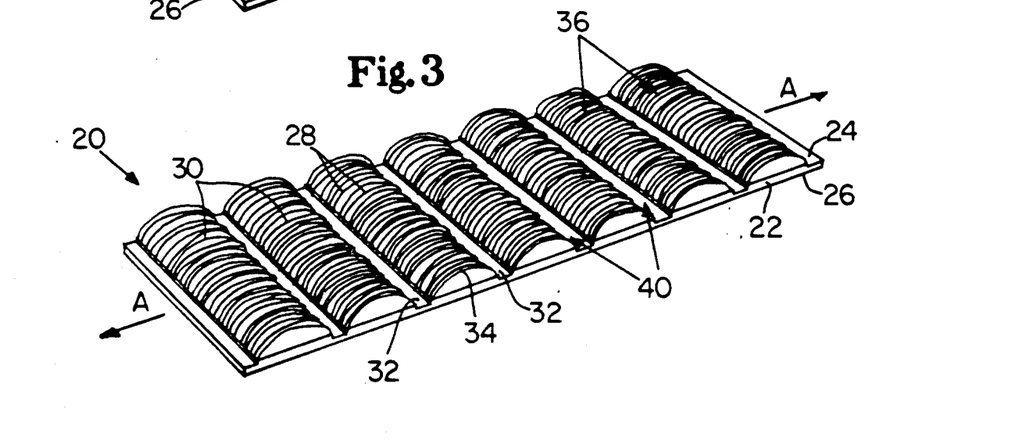
FIG. 3 is a perspective view of a loop fastening material of the present invention when the backing is in its dimensionally stable state.

Referring to the drawings, FIG. 3 shows a preferred embodiment, loop fastening material 20, of the present invention. As used herein, the term "loop fastening material" refers to the portion of a hook and loop-type fastening device that is designed to engaged the engaging elements of a complementary hook fastening material. Thus, a loop fastening material may also be referred to as the female fastener, the loop fastener or the fibrous fastening material.

As shown in FIG. 3, the loop fastening material 20 comprises a backing 22 of an orientable material, preferably a heat-shrinkable material shown in its heat stable state in FIG. 3, having a first surface 24 and a second surface 26, and a multiplicity of fibrous elements 28 extending outwardly from the first surface 24 of the backing 22. The fibrous elements 28 are formed from filaments 30 positioned on and secured to the backing 22. The filaments 30 are intermittently secured to the backing 22 at spaced, fixed regions 32 along the length of each filament 30, while the heat shrinkable material of the backing 22 is in its heat unstable state, the fixed regions 32 defining between each pair an unsecured catching region 34.

The filaments 30 are preferably positioned on the backing 22 essentially parallel to the path of response of the orientable material, designated by the line A—A in FIG. 3, and in parallel with each other. The filaments 30 are continually secured to the backing 22 across the filaments 30 and preferably along essentially the entire width of the backing 22 in a direction essentially perpendicular to the path of response and at regularly spaced intervals to form loop tunnels 36. Thus, each loop tunnel 36 preferably comprises a multiplicity of parallel fibrous elements 28.

Figure 1:
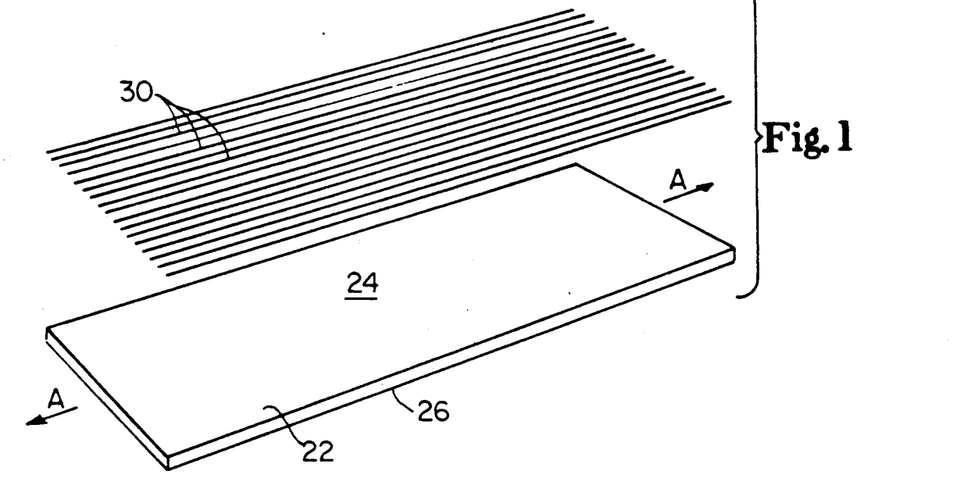
FIG. 1 is a perspective view of the filaments and the backing used to form the present invention prior to the filaments being positioned or laid down on the backing.

FIG. 1 shows the backing 22 and the filaments 30 used to form the loop fastening material 20 prior to their association. The heat shrinkable material used for the backing 22 is in its heat unstable state prior to the filaments 30 being positioned or laid down on the backing 22. (While the orientable material could be in its dimensionally stable state when the filaments 30 are positioned on the backing 22, this is not preferred because in causing the orientable material to be transformed to its unstable state, filaments 30 may be dislocated, disarranged, skewed or bonded into the backing 22 such that the fibrous elements would not be as effective in engaging the hook fastening material.) Thus, the filaments 30 are preferably positioned on the backing 22 while the orientable material of the backing 22 is in its heat unstable state and while the filaments 30 are in an untensioned condition so that when the orientable material is caused to contract to its stable state, the filaments 30 are shirred at the unsecured catching regions 34 to form the fibrous elements 28 of the present invention. The filaments 30 are positioned on the backing 22 in a direction essentially parallel to the path of response of the heat-shrinkable material and preferably in parallel with each other.

Figure 2:
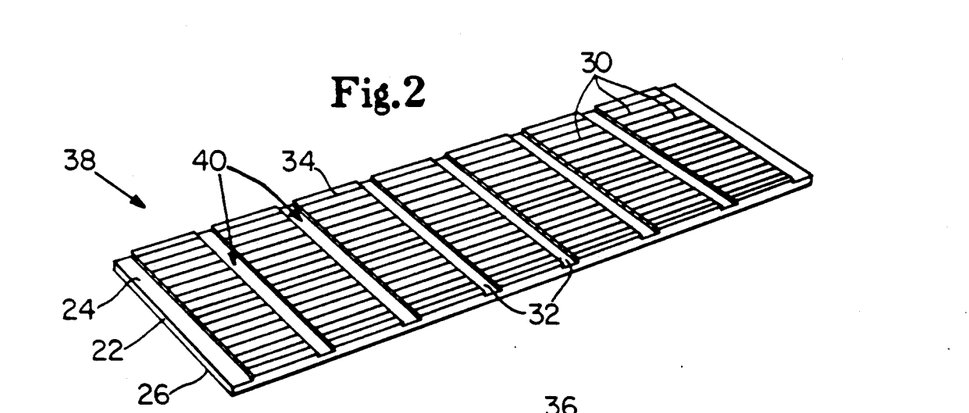
FIG. 2 is a perspective view of a loop fastening material of the present invention when the backing is in its dimensionally unstable state.

FIG. 2 shows a preferred embodiment of the loop fastening material 20 when the heat-shrinkable material is in its heat unstable state (dimensionally unstable state) and after the filaments 30 have been positioned on and secured to the backing 22. The filaments 30 are preferably intermittently secured to the backing 22 at the spaced, fixed regions 32 to form the unsecured catching regions 34 therebetween. The filaments 30 are continually secured across themselves to the backing 22, and preferably along essentially the entire width of the backing 22, in a direction essentially perpendicular to the path of response of the heat-shrinkable material at regularly spaced intervals to form uniform width catching regions 34. As shown in FIGS. 2 and 3, the filaments 30 are secured to the backing 22 by ultrasonically welding the material together at unitary zones of attachment 40.

The resultant composite material 38 shown in FIG. 2 is then caused to be transformed to its heat stable state (dimensionally stable state). Since the backing 22 is a heat-shrinkable material, the composite 38 is preferably heated, although the orientable material can be caused to be transformed to its dimensionally unstable state in many ways including irradiating the material or releasing the tension forces applied to the material. The heating of the composite 38 allows the heat-shrinkable material to contract to and regain its heat stable state along the path of response. As a result of the contraction or shrinkage of the backing 22, the filaments 30 are shirred or gathered at the catching regions 34 to form the fibrous elements 28 and the loop tunnels 36 as shown in FIG. 3 extending from the first surface 24 of the backing 22.

The backing 22 of the loop fastening material 20 provides a strong base or foundation on or into which the filaments 30 are positioned and secured, and that can cause the filaments 30 to be shirred to form fibrous elements 28. Thus, in the present invention the backing 22 comprises an orientable material capable of exhibiting a dimensionally stable state and a dimensionally unstable state and having a path of response along which the orientable material is transformed from its unstable state to its stable state. While the backing 22 is shown in FIGS. 1-3 to preferably comprise only the orientable material, it should be understood that the backing 22 may also comprise any other suitable materials secured to the orientable material so long as such layer or layers of material are flexible so that they do not inhibit the shirring of the filaments 30 as the orientable material is allowed to contract to its stable state. Thus, for example, webs or films of material may be bonded, laminated or otherwise secured to the orientable material to form a composite backing so as to provide a stronger backing or a backing that is more compatible for bonding to the filaments or to the article onto which the loop fastening material 20 will be placed. Examples of such suitable materials include nonwovens, wovens, polyethylene films, or any other materials known in the art and suitable for such backing. As previously discussed, the backing 22 is preferably an ethyl vinyl acetate copolymer.

The fibrous elements 28 of the present invention securely engage the engaging elements of a complementary hook fastening material to provide a fastening device. The fibrous elements 28 each preferably comprise the loop structure shown in FIG. 3 having a pair of spaced, fixed regions 32 and an unsecured catching region 34 between the pair of fixed regions 32. While the fibrous elements 28 may have shapes other than the loop structure shown in FIG. 3, such shapes are not preferred.

The fibrous elements 28 of the present invention are preferably formed by filaments 30 positioned on and secured to the backing 22. As used herein, the term "filament" defines a member having a high ratio of length to diameter or width. Thus, a filament may be a fiber, a thread, a strand, a yarn or any other member or combination of these members, including filaments that are preattached together in woven or nonwoven webs, as are known in the art. Suitable materials for such filaments include natural fibers such as cotton or wool; synthetic fibers of nylon, polyamides, polyesters or polyolefins; spun yarns; polyethylene fibers; polypropylene fibers; nylon fibers; non-woven webs; or any other material or combination of materials known in the art and suitable for use herein. It should be noted that in the preferred embodiment, the material used for the filaments 30 should not have a melting temperature lower than the temperature at which the orientable material is heat shrunk nor should the filaments 30 be heat-shrinkable at or below such temperature. In addition, the filaments 30 may be manufactured using a number of manufacturing techniques including those such that the filaments are spun, blown or the like. Preferably, each filament 30 is a polypropylene fiber of 8 or 9 denier included in a spunbounded nonwoven web such as manufactured by James River Corporation under the tradename Celestra.

The filaments 30 of the present invention are preferably continuous filaments. As used herein, the term "continuous filaments" refers to relatively long filaments that provide a minimum of loose ends in the central region of the backing. If the filaments 30 are not continuous filaments but are short or staple, then the ends of the staple filaments could be positioned as a portion of the catching regions 34 of the fibrous element 28 such that a complete fibrous element 28 having two fixed regions 32 and a catching region 34 would not be formed. The resulting incomplete fibrous element 28 would not be able to securely engage the engaging elements of a hook fastening material such that the ability of the loop fastening material to provide a secure closure would be diminished. Thus, although short or staple fibers are contemplated for use in the present invention, continuous filaments 30 are preferred. A preferred continuous filament 30 has a length to make at least one complete fibrous element 28 and most preferably has a length such that the ends of the continuous filament 30 are either disposed at a fixed region 32 or adjacent the terminating edge of the backing 22.

While each fibrous element 28 is preferably formed from a single filament 30, the fibrous elements 28 may be formed from a segment of that filament 30 or the whole filament 30 depending upon the size, strength and manufacturing ease required to make the fibrous elements 28 to securely engage the hook fastening material. Thus, for example, the filament 30 may only have a pair of fixed regions 32 positioned adjacent its ends so that the fibrous element 28 is formed of a whole filament 30. Preferably, the filament 30 has a number of fixed regions 32 positioned along its length to form a plurality of fibrous elements 28 along each filament 30.

The filaments 30 are positioned on the backing 22 preferably while the orientable material of backing 22 is in the dimensionally unstable state and while the filaments 30 are in an untensioned condition. (While the filaments 30 could conceivably be positioned on the backing in a tensioned or unstable state, such is not preferred to provide for maximum shirring of the filaments.) The configuration in which the filaments 30 are positioned or laid down on the backing 22 determines the size and the ability of the loop fastening material 20 to provide an effective fastening device. While the filaments 30 may be randomly positioned on the backing 22 such that filaments 30 overlap or extend in many different directions, it has been found that the filaments 30 should preferably be positioned as parallel with each other as possible to provide fibrous elements 28 configured in a uniform direction. In addition, while the filaments 30 may be positioned lengthwise on the backing 22 in any direction, in order to take advantage of the maximum shirring effect of the orientable material of the backing 22 and to form fibrous elements 28 of maximum height, the filaments 30 are preferably positioned on the backing 22 in a direction essentially parallel to the path of response of the orientable material. "Essentially parallel" is used herein to indicate that the filaments 30 need not extend absolutely parallel to the path of response so long as a majority of the filaments 30 extend parallel or a small deviation off of parallel to the path of response. The filaments 30 may be positioned or laid down on the backing 22 by any method or means as is known in the art.

Either after the filaments 30 have been positioned on the backing 22 or simultaneously with the filaments 30 being positioned on the backing 22, the filaments 30 are secured to the backing 22. The filaments 30 are secured to the backing 22, while the orientable material of the backing 22 is in its dimensionally unstable state, intermittently at spaced, fixed regions 32 along the length of the filaments 30 and preferably continually across a number or all of the filaments 30 (along the width of the backing 22). The filaments 30 may be secured to the backing 22 by any method or means as is known in the art. For example, the filaments 30 may be adhesively secured with hot melt adhesives, glues, pressure sensitive adhesives or any other adhesive material as is known in the art. In addition, the filaments 30 may be heat/pressure sealed into the backing 22. Preferably, the filaments 30 are ultrasonically welded to the backing 22 by ultrasonic means as are known in the art. A method of and apparatus for ultrasonically welding two webs together is described in U.S. Pat. No. 4,531,999 issued to Persson et al. on Jul. 30, 1985 and is incorporated herein by reference.

The filaments 30 are secured to the backing 22 intermittently along the length of each of the filaments to form the spaced, fixed regions 32. Intermittent securement being used to define alternating regions of securement (fixed regions 32) and nonsecurement (catching regions 34) at either regularly or irregularly spaced intervals.

The fixed regions 32 can be spaced apart at intervas of any dimension depending upon the size of the engaging elements of the hook fastening material and the height of the fibrous element 28 required to provide the necessary shear and peel resistance. They are preferably regularly spaced, but they can be irregularly spaced. They are preferably regularly spaced at intervals of about 0.5 mm to about 25 mm, more preferably about 2 mm to about 5 mm, as measured from center to center when the orientable material is in its heat stable state.

While each individual filament 30 could be secured to the backing 22 at fixed regions 32 along the filament 30 that are positioned at intervals different from the fixed regions of each adjacent filament, as shown in FIGS. 2 and 3 the filaments 30 are preferably secured continually across a plurality of or all of the filaments 30. Continually secured is used in this context to mean that a number of adjacent filaments 30 are secured to the backing 22 along a line (straight or curvilinear) across the filaments (across the width of the filaments) so that the fixed regions of one filament are adjacent the fixed regions of an adjacent filament. The term "across the filaments" refers to an orientation generally in the direction of the width of the filaments or transverse to the length of the filaments. Continual securement is preferred so that the fibrous elements 28 formed are uniform and so that the loop tunnels 36 of the present invention are formed. Such continual securement is also preferred because such a loop fastening material 20 is less expensive to produce because of the speed increase obtainable in manufacturing such a loop fastening material. The filaments 30 may be continually secured to the backing in any pattern or combination of patterns to provide loop tunnels 36 of differing lengths, widths or a pattern of varying loop tunnels 36. The filaments 30 are preferably continually secured across the filaments in at least spaced segments and most preferably along essentially the entire width of the backing 22 for ease of manufacture and uniformity of the loop tunnels 36. The term "along essentially the entire width" is used in this context to indicate that the continuous bonds need not extend absolutely across the entire width of the backing 22.

The filaments 30 are also preferably continually secured in a straight line across the filaments 30 in a direction essentially perpendicular to the path of response of the backing 22. The term "essentially perpendicular" to the path of response refers to an orientation generally perpendicular but not absolutely perpendicular to the path of response. As illustrated, the fixed regions 32 are shown to be positioned at essentially right angles to the longitudinal dimension of the backing 22. One can, however, depart from the perpendicular orientation without departing from the scope and spirit of this invention. Thus, the filaments 30 may be continually secured at an angle to the perpendicular. However, it is believed that the departure from the perpendicular may become too great for practical operation of the present invention when the angle from the perpendicular exceeds about 45°. In FIGS. 2 and 3, the filaments 30 are preferably shown as being continually secured at regularly spaced, fixed regions 32 positioned essentially perpendicular to the path of response of the backing 22.

The filaments 30 are preferably ultrasonically welded to the backing 22. The ultrasonic welding pattern may comprise unitary zones of attachment or discrete spaced zones of attachment. For example, the spaced zones of attachment could be circular or elliptical shapes as are shown in U.S. Pat. No. 4,515,595 issued to Kievit et al. on May 7, 1985 and which is incorporated herein by reference. Preferably, however, the welding pattern comprises unitary zones of attachment 40 as are shown in FIGS. 2 and 3.

An exemplary embodiment of the loop fastening material 20 comprises a backing 22 of a material of a blend of ethylene propylene rubber with ethyl vinyl acetate having a multiplicity of continuous, 9 denier, polypropylene filaments 30 positioned on and secured to the backing 22. The filaments 30 are positioned parallel to each other and in a direction essentially parallel to the path of response of the backing 22. The filaments 30 are continually ultrasonically welded to the backing 22, while the backing 22 is in its heat unstable state, at unitary zones of attachment 40 at regularly spaced intervals of about 2.5 mm (about 0.1 inches) along the filaments 30 and across the filaments along the entire width of the backing 22 in a straight line positioned at an angle that is essentially perpendicular to the path of response. After the resultant composite material has been heated to cause the heat shrinkable material to contract along its path of response to its heat stable state, the filaments 30 are shirred at the unsecured catching regions 34 to form a multiplicity of fibrous elements 28 and a plurality of loop tunnels 36 on the backing 22.

Figure 4:
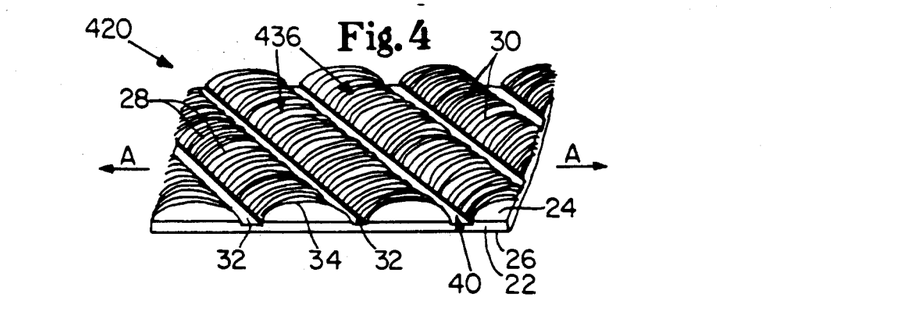
FIG. 4 is a perspective view of an alternative embodiment of a loop fastening material of the present invention.

FIG. 4 shows an alternative embodiment, loop fastening material 420, of the present invention. The loop fastening material 420 of FIG. 4 is similar to that shown in FIG. 3 except that the filaments 30 are continually secured at an angle to the perpendicular of the path of response of the orientable material. Such a loop fastening material 420 thus has a number of loop tunnels 436 disposed on the backing 22 at an angle to the edges of the backing 22. Such a loop fastening material 420 is believed to be especially effective for engaging hook fastening materials wherein the engaging elements are disposed in a regularly spaced pattern such that a complete row of engaging elements engage different loop tunnels 436 and are not disposed completely at a fixed region 32.

Figure 5:
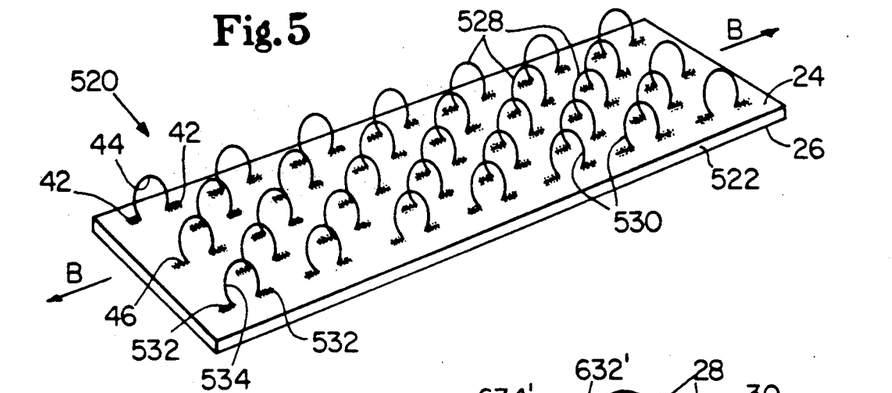
FIG. 5 is a perspective view of a further alternative embodiment of a loop fastening material of the present invention.

FIG. 5 shows an alternative embodiment, loop fastening material 520, of the present invention. The backing 522 of the loop fastening material 520 comprises an elastomeric material such as an elastic member of natural rubber such as is marketed by Easthampton Rubber Thread Company. The elastomeric material has an elongated orientation (not shown), a relaxed orientation (shown in FIG. 5), and a path of response, line B—B, along which the elastomeric material contracts when tension is released from the backing 522. The fibrous elements 528 of the loop fastening material 520 each comprise a whole filament 530 in which the spaced, fixed regions 532 are located adjacent the ends 42 of the filament 530 such that the unsecured catching region 534 comprises the middle portion 44 of the filament 530. A preferred filament 530 used for the loop fastening material 520 is a spun thread of a cotton blend such as an ordinary sewing thread as is well known.

The loop fastening material 520 is formed by applying tensional forces to the backing 22 in any manner along the axis of the desired path of response and then positioning and securing the filaments 530 to the backing 522 while the backing 522 is in this elongated orientation. Each of the filaments 530 are randomly positioned on the backing 522 in a preferred direction essentially parallel to the path of response. The filaments 530 are adhesively secured on the backing 522 at the fixed regions 532 by applying a hot melt adhesive 46 to the ends of the filaments 530. After the adhesive 46 is allowed to set up, the tensional forces are removed and the backing 522 is allowed to contract to its relaxed orientation, the fibrous elements 528 being formed by the shirring of the filaments 530 at the catching regions 534. After the fibrous elements 528 are formed, the elastomeric material is preferably stabilized so that the elastomeric material will resist re-elongation during use that would otherwise distort the fibrous elements 528. The elastomeric material may be stabilized by any means or by a method such as by attaching it to a relatively nonelastic member or material.

Figure 6:
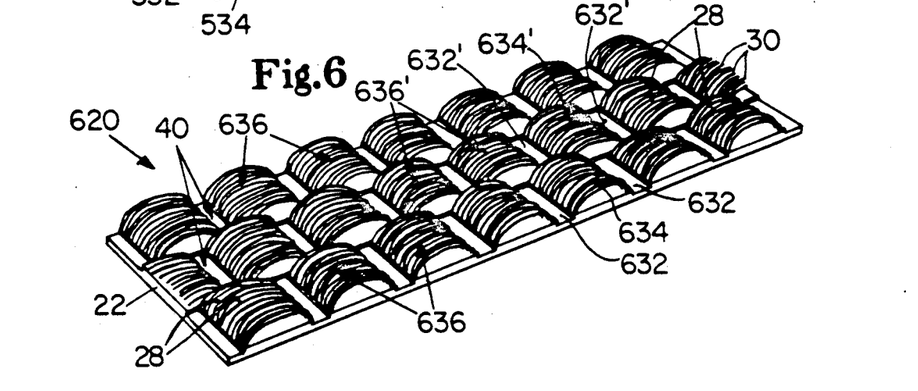
FIG. 6 is a perspective view of a still further alternative embodiment of a loop fastening material of the present invention.

FIG. 6 shows a further alternative embodiment, loop fastening material 620, of the present invention. The loop fastening material 620 has a plurality of loop tunnels 636 and 636' disposed in a discrete spaced pattern across the width of the backing 22. In the particular embodiment, the loop tunnels are positioned in an evenly staggered pattern wherein the fixed regions 632 of one row of loop tunnels 636 are positioned in the center of the catching regions 634' of the adjacent rows of loop tunnels 636'.

Figure 7:
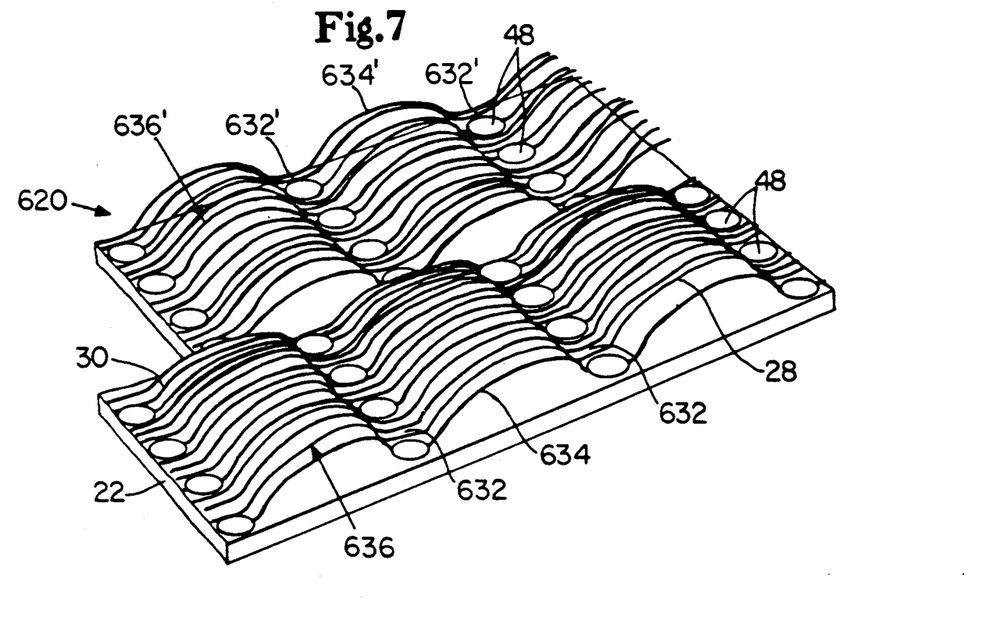
FIG. 7 is an enlarged fragmentary perspective view of the loop fastening material of FIG. 6 showing the ultrasonic welds.

FIG. 7 shows an enlarged view of a portion of the loop fastening material 620 while the backing 22 is in its heat stable state. As shown, the filaments 30 are ultrasonically welded to the backing 22 at spaced evenly staggered, fixed regions 632 and 632'. The fixed regions 632 and 632' are evenly spaced such that the fixed regions 632 and 632' are evenly staggered. The fixed regions 632 and 632' are ultrasonically welded at discrete zones of attachment 48 in a circular shape.

Figures 8, 9, 10:
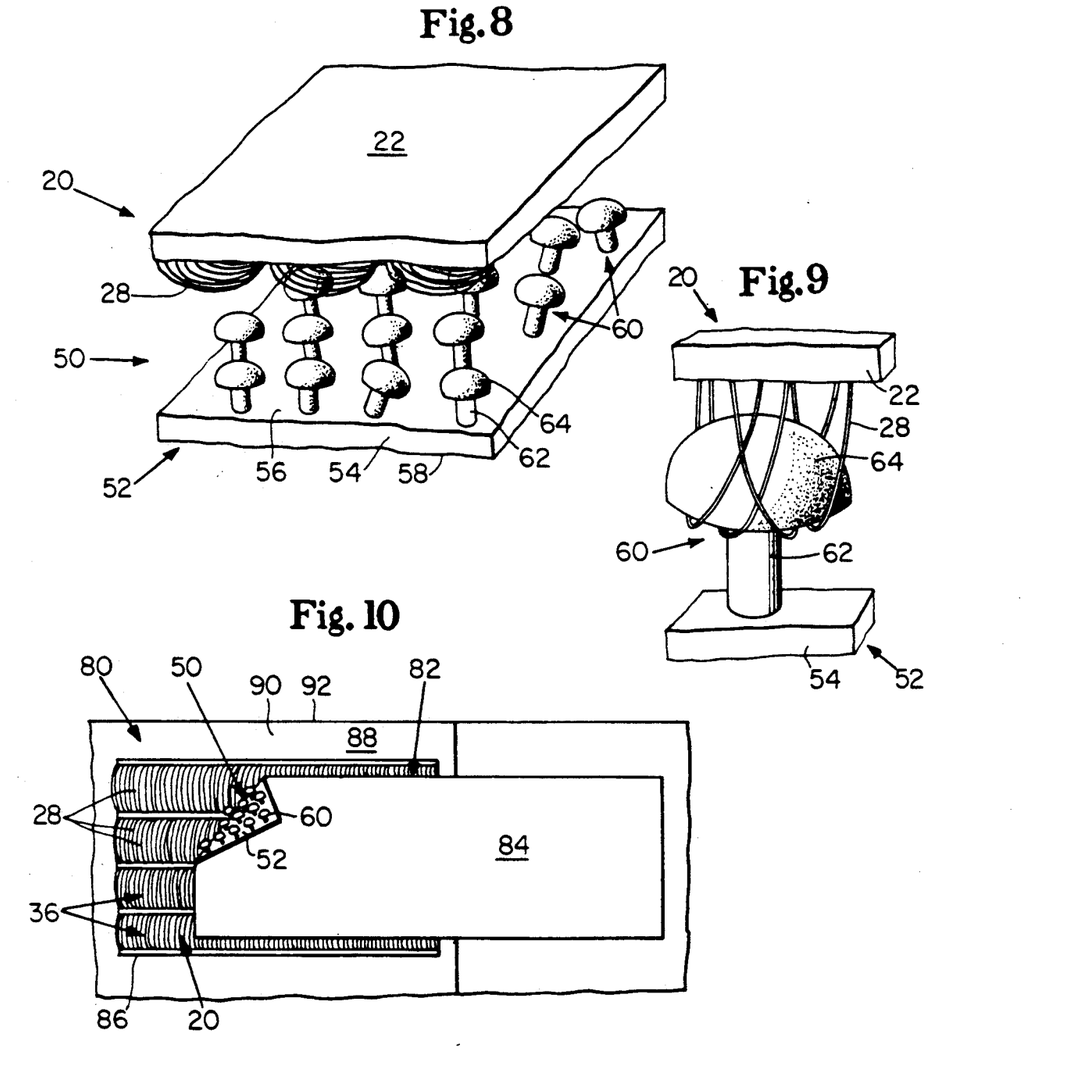
FIG. 8 is a perspective view of a fastening device according to the present invention.
FIG. 9 in an enlarged side view of an engaging element of a hook fastening material engaged with the fibrous elements of a loop fastening material of the present invention.
FIG. 10 is an enlarged perspective view of a tape fastening system of a disposable diaper incorporating the loop fastening material of the present invention.

FIG. 8 shows a preferred fastening device 50 of the present invention. The fastening device 50 preferably comprises the loop fastening material 20 of the present invention and a complementary hook fastening material 52 engageable with the fibrous elements 28 of the loop fastening material 20. As used herein, the term "hook fastening material" is used to designate the portion of the fastening device 50 having engaging elements. Thus, the hook fastening material may also be referred to as the male fastener. It should also be understood that the use of the term "hook" should be nonlimiting in the sense that the engaging elements may comprise any shape as is known in the art so long as they are adapted to engage a complementary loop fastening material. As shown, the hook fastening material 52 preferably comprises a base 54 having a first surface 56 and a second surface 58 and a plurality of engaging elements 60 extending from the first surface 58 of the base 54. Each of the engaging elements 60 are shown to preferably comprise a stem 62 supported at one end on the base 54 and an enlarged head 64 positioned at the end of the stem 62 opposite of the base 54.

The hook fastening material 52 may be manufactured from a wide range of materials. Such suitable materials include nylon, polyester, polypropylene or any combination of these or other materials. A suitable hook fastening material 52 comprises a number of shaped engaging elements projecting from a woven backing such as the commercially available material designated "Scotchmate" brand No. FJ3402 available from Minnesota Mining and Manufacturing Company, St. Paul, Minn. Alternatively, the engaging elements may have any other shape such as hooks, "T's", or any other shape as are well known in the art. A particularly preferred hook fastening material is described in copending U.S. patent application Ser. No. 07/007,841 entitled "Disposable Diaper Having An Improved Fastening Device" filed Jan. 26, 1987 by C. L. Scripps and which is incorporated herein by reference.

In use, the hook and loop fastening materials are pressed face to face against each other so that the fibrous elements 28 of the loop fastening material 20 "catch" on the engaging elements 60 of the hook fastening material 52. With the fibrous elements 28 thus "hooked" or caught by the engaging elements 60 as is shown in FIG. 9, the connection between the elements resists sheer stress and certain peel forces applied to the fastening device 50. The fastening device 50 is separated by peeling the hook fastening material 52 away from the loop fastening material 20 such that the fibrous elements 28 are released, or broken, or the bonds of the fixed regions 32 break. Thus, the hook fastening material 52 is completely detached from the loop fastening material 20.

The fastening device 50 of the present invention has been found to be especially useful for providing a fastening device for disposable articles. The loop fastening material can be made relatively inexpensively in comparison to the woven loops used in known fastening devices. In addition, since the fastening device on a disposable article is opened and closed far fewer times than on reuseable articles, the loop fastening material is more suited for disposable articles since it need only be strong enough to provide a limited number of secure closures (10-20 times). It should be noted, however, that the loop fastening material can be made much stronger for use on durable articles or for any other contemplated use by, for example, increasing the diameter or denier of the filaments, more strongly securing the filaments to the backing or increasing the density of the fibrous elements relative to the number of engaging elements. (However, these changes also increase the cost of such loop fastening materials.) Thus, the fastening device 50 is especially useful on such disposable articles as packaging, disposable absorbent articles, disposable wraps or any other disposable material.

As shown in FIG. 10, the fastening device 50 is preferably positioned on a disposable absorbent article such as a disposable diaper 80. The disposable diaper 80 preferably comprises a liquid pervious topsheet, an absorbent core, a liquid impervious backsheet and elastic members. While the topsheet, the absorbent core, the backsheet and the elastic members may be assembled in a variety of well known configurations, a preferred disposable diaper configuration is described in U.S. Pat. No. 3,860,003 entitled "Contractible Side Portions For Disposable Diapers" which issued to K. B. Buell on Jan. 14, 1975 and which patent is incorporated herein by reference.

As shown in FIG. 10, the tape fastening system 82 of the diaper 80 preferably comprises the fastening device 50 of the present invention. Any of the well known configurations and constructions may be used as the tape fastening system. A preferred tape fastening system is a Y-tape as described in detail in U.S. Pat. No. 3,848,594 entitled "Tape Fastening System For Disposable Diaper" which issued to K. B. Buell on Nov. 19, 1974 and which patent is incorporated herein by reference. Alternatively preferred tape fastening systems are described in detail in co-pending U.S. patent application Ser. No. 821,100 entitled "Disposable Diaper Having Wide Tapered Fastening Tapes" filed Jan. 21, 1986 by H. R. Burkhart and K. B. Buell; U.S. patent application Ser. No. 842,326 entitled "Disposable Diaper Having An Improved Side Closure" filed Mar. 21, 1986 by J. W. Toussant and M. H. Hasse; and previously referenced co-pending U.S. patent application Ser. No. 07/007,841 filed Jan. 26, 1987 by C. L. Scripps; all of which are incorporated herein by reference.

The preferred tape fastening system illustrated in FIG. 10 has a tape tab 84 and a second member 86. Preferably, the tape tab 84 comprises the hook fastening material 52 having the engaging elements 60 extending from the tape tab 84. The second member 86 preferably is disposed on the outside surface 88 of the waist portion 90 of the diaper 80. In the preferred embodiment of the disposable diaper 80, the loop fastening material 20 of the present invention comprises the second member 86. As shown, the loop fastening material 20 preferably is oriented on the second waist portion 90 of the diaper 80 with the loop tunnels 36 extending essentially parallel to the end edge 92 of the diaper 80. (Parallel to the direction of shear forces applied to the fastening device during use.) Thus, in this configuration the fibrous elements 28 provide the maximum peel and shear force resistance. The loop fastening material 20 may, however, be oriented on the second waist portion 90 in any configuration such as with the loop tunnels 36 extending perpendicular to the end edge 92 of the diaper 80 or at any angle to the end edge 92.

While particular embodiments of the present invention have been illustrated and described, it would be obvious to those skilled in the art that various other changes and modifications can be made without departing from the spirit and scope of the invention. It is therefore intended to cover in the appended Claims all such changes and modifications that are within the scope of this invention.

What is claimed is:

1. A disposable absorbent article comprising a liquid pervious topsheet, a liquid impervious backsheet associated with said topsheet, an absorbent core positioned between said topsheet and said backsheet, and a fastening device positioned on the disposable absorbent article. said fastening device comprising a loop fastening material capable of engaging a complementary hook fastening material, said hook fastening material comprising a base and a plurality of engaging elements extending from said base, said loop fastening material comprising a backing of orientable material having a dimensionally unstable state, a dimensionally stable state, and a path of response along which said material has been contracted from the unstable state to the stable state; and a multiplicity of fibrous elements extending from said backing, said fibrous elements comprising filaments that were positioned on said backing and secured to the surface of said backing while said orientable material was in its unstable state, said filaments being secured to said backing at spaced, fixed regions along the length of each of said filaments to define between each pair of fixed regions an unsecured catching region, wherein said fibrous elements comprise those filaments which have been shirred when said orientable material was contracted to its stable state.

2. The disposable absorbent article of claim 1 wherein said filaments are positioned parallel to each other on said backing.

3. The disposable absorbent article of claim 2 wherein said filaments are positioned on said backing essentially parallel to the path of response of said orientable material.

4. The disposable absorbent article of claim 1 wherein said filaments are randomly positioned on said backing.

5. The disposable absorbent article of claim 1 wherein said filaments are continually secured across said filaments.

6. The disposable absorbent article of claim 5 wherein said filaments are secured across said filaments in spaced segments.

7. The disposable absorbent article of claim 1 wherein said filaments are secured to said backing in an evenly staggered pattern.

8. The disposable absorbent article of claim 5 wherein said filaments are secured across said filaments along essentially the entire width of said backing.

9. The disposable absorbent article of claim 1 wherein said filaments are secured to said backing essentially perpendicular to the path of response of said orientable material.

10. The disposable absorbent article of claim 1 wherein said filaments are secured to said backing at an angle to the direction perpendicular to the path of response of said orientable material.

11. The disposable absorbent article of claim 1 wherein said filaments are adhesively secured to said backing.

12. The disposable absorbent article of claim 1 wherein said filaments are heat/pressure sealed to said backing.

13. The disposable absorbent article of claim 1 wherein said filaments are ultrasonically welded to said backing.

14. The disposable absorbent article of claim 13 wherein said filaments are ultrasonically welded at unitary zones of attachment.

15. The disposable absorbent article of claim 13 wherein said filaments are ultrasonically welded at discrete spaced zones of attachment.

16. The disposable absorbent article of claim 1 wherein said orientable material comprises an elastomeric material.

17. The disposable absorbent article of claim 1 wherein said orientable material comprises a heat shrinkable material.

18. The disposable absorbent article of claim 17 wherein said orientable material comprises a heat shrinkable polymer.

19. The disposable absorbent article of claim 18 wherein said heat shrinkable polymer is an ethylene vinyl acetate copolymer.

20. The disposable absorbent article of claim 1 wherein said filaments are continuous.

21. The disposable absorbent article of claim 20 wherein said filaments are threads.

22. The disposable absorbent article of claim 21 wherein said filaments are polypropylene fibers.

23. The disposable absorbent article of claim 1 wherein each of said filaments forms a fibrous element.

24. The disposable absorbent article of claim 1 wherein each of said filaments forms a plurality of fibrous elements.

25. The disposable absorbent article of claim 1 wherein each of said filaments forms a plurality of fibrous elements such that a plurality of loop tunnels are formed on said backing.

26. The disposable absorbent article of claim 1 wherein said orientable material comprises a heat shrinkable material, said filaments comprise continuous fibers that are positioned on said backing essentially parallel to the path of response of said orientable material and are ultrasonically welded to said backing continuously across said filaments in a direction essentially perpendicular to the path of response of said orientable material and across essentially the entire width of said backing.

27. The disposable absorbent article of claim 26 wherein each of said shirred filaments forms a plurality of fibrous elements such that a plurality of loop tunnels are formed on said backing.

28. The disposable absorbent article of claims 26 or 27 wherein said filaments are polypropylene fibers.

29. A disposable diaper comprising:
a liquid pervious topsheet;
a liquid impervious backsheet associated with said topsheet;
an absorbent core positioned between said topsheet and said backsheet; and
a tape fastening system comprising
a) a tape tab comprising a hook fastening material having a base and a plurality of engaging elements extending from said base; and
b) a second member disposed on the outside surface of said backsheet, said second member comprising a loop fastening material capable of engaging said hook fastening material, said loop fastening material comprising
i) a backing of orientable material having a dimensionally unstable state, a dimensionally stable state, and a path of response along which said backing has been contracted from the unstable state to the stable state; and
ii) a multiplicity of fibrous elements extending from said backing, said fibrous elements comprising filaments that were positioned on said backing and secured to the surface of said backing, while said backing was in its unstable state, said filaments being secured to said backing at spaced, fixed regions along the length of each of said filaments to define between each pair of fixed regions an unsecured catching region, wherein said fibrous elements comprise those filaments which have been shirred when said orientable material was contracted to its stable state.

30. The disposable diaper of claim 29 wherein said filaments are continually secured across said filaments along essentially the entire width of said backing.

31. The disposable diaper of claim 30 wherein said filaments are secured to said backing essentially perpendicular to the path of response of said backing.

32. The disposable diaper of claim 31 wherein each of said filaments forms a plurality of fibrous elements such that a plurality of loop tunnels are formed on said backing.

33. The disposable diaper of claim 32 wherein said loop fastening material is oriented on the disposable absorbent article such that said loop tunnels extend essentially parallel to the end edge of the diaper.

34. The disposable diaper of claim 33 wherein said backing comprises a heat shrinkable material.

35. The disposable diaper of claim 34 wherein said filaments are ultrasonically welded to said backing.

36. The disposable diaper of claim 34 wherein said filaments are adhesively secured to said backing.

37. The disposable diaper of claim 34 wherein said filaments are heat/pressure sealed to said backing.

* * * * *